United States Patent [19]

Pak

[11] Patent Number: 4,888,182

[45] Date of Patent: Dec. 19, 1989

[54] COMPOSITIONS AND METHODS OF TREATING CALCIUM RENAL STONES

[75] Inventor: Charles Y. C. Pak, Dallas, Tex.

[73] Assignee: Board of Regents of the University of Texas System, Austin, Tex.

[21] Appl. No.: 19,056

[22] Filed: Feb. 26, 1987

Related U.S. Application Data

[63] Continuation-in-part of Ser. No. 741,715, Jun. 6, 1985, abandoned, which is a continuation of Ser. No. 483,678, Apr. 11, 1983, abandoned.

[51] Int. Cl.⁴ .............................................. A61K 31/14
[52] U.S. Cl. ................................... 424/677; 424/464; 514/891
[58] Field of Search ...................... 424/127, 464, 677; 514/891

[56] References Cited

U.S. PATENT DOCUMENTS

| | | | |
|---|---|---|---|
| 3,624,205 | 11/1971 | Hitchings et al. | 514/258 |
| 4,221,783 | 9/1980 | Puscas et al. | 424/127 |
| 4,289,750 | 9/1981 | Kopp et al. | 424/33 |
| 4,405,596 | 9/1983 | Helbig et al. | 424/33 |

OTHER PUBLICATIONS

Packett, et al. (1968) *J. Animal Science* 27:1716–1721.
Sherman et al, (1936), J. Biol. Chem., 113:265–271.
Chapter by Forbes and Demsey, Diseases of the Kidney, Strauss and Welt (ed.), Little Brown & Co. (1963).
Gutman and Yu, Am. J. Med. (1968), 45:756.
Peacock et al., (1968), British Medical Journal, 2:729–731.
Parfitt, Arch. Intern. Med. (1969), 124:736–740.
Pak et al., Proc. Soc. Exp. Biol. Med. (1969), 130:753–757.
Pytel' IUA, et al., (1973), Urol. Nefrol. (Mosk), 37:28–33.
Baruch et al., Med. Clin. N. Am. (1975), 59:569–582.
Coe et al., Proc. Soc. Exp. Biol. Med., (1975), 149:926–929.
Pak et al., Proceedings of the Society for Experimental Biology and Medicine, 149:930–932.
Pak et al., Proc. Soc. Exp. Biol. Med. (1976), 153:83–87.
Pak et al., (1977), J. Clin. Invest., 59:426–431.
Petritsch, Urology (1977), X:536–538.
Reference from Physicians' Desk Reference (1977).
Bisaz et al., Mineral Electrolyte Metab. (1978), 1:74–83.
Henneman, (Jan. 1978), Modern Medicine.
Robson and Heading, Postgraduate Medical Journal, (1978), 54:36–37.
Resnick, Urology Rounds (1979), 1:3.
Smith, Strauss and Welt's Diseases of the Kidney, (1979), Early and Gottschalk, eds., Boston: Little Brown and Co., pp. 893–930.
Pak et al., Investigative Urology, (1979), 17:138–140.
Butz and Dulce, Urolithiasis Clinical and Basic Research (1980), Robertson et al. eds., Plenum Press, London, pp. 881–884.
Butz and Rost, 5th Symp. on Exptl. Urol., p. 243, (1980).
Hartung et al., 5th Symp. on Exptl. Urol, p. 243, (1980).
Pak et al., Amer. J. Med., (1980), 69:19–30.
Pak et al., Mineral and Electrolyte Metabolism, (1980); 4:130–136.

(List continued on next page.)

*Primary Examiner*—John W. Rollins
*Attorney, Agent, or Firm*—Arnold, White & Durkee

[57] ABSTRACT

Methods and compositions useful for the treatment and prophylaxis of calcium renal stones are disclosed. The methods involve administering potassium citrate compositions to persons afflicted with or susceptible to calcium renal stone formations. A typical dosage scheme involves administering about 30 to 120 meq potassium citrate per day in divided doses. Such treatments are effective in dissolving existing calcium stones and preventing formation of new calcium stones. Moreover, the results of a comparative clinical assay indicate the potassium citrate is superior to sodium citrate in the treatment of uric acid lithiasis. Potassium citrate therapy averts calcium renal stone formation, a complication which is often associated with sodium citrate or sodium bicarbonate alkalinization therapy.

13 Claims, 5 Drawing Sheets

OTHER PUBLICATIONS

Rudman et al., New Eng. J. Med., (1980), 303:657.
Coe, Manual of Nephrology: Diagnosis and Therapy (1981), Schrier ed., Boston Little and Brown, pp. 85–97.
Leskovar et al., Urol. Int. (1981), 36:325.
Pak, Cecil's Textbook of Medicine, (1981), Wyngarden and Smith eds., Philadelphia, pp. 584–588.
Pak et al., Contr. Nephrol. (1982), 33:136–151.
Sakhaee et al., (1982), Clinical Research, 30:403A.
Pak, Journal of Urology, (1982), 128:1157–1164.
Nicar et al., Urology, (1983), 21:8–14.
Pak et al., Trans. Assoc. Amer. Physic., (1983), 96:294–305.
Sakhaee et al., Kidney International, (1983), 24:348–352.
Nicar et al., J. Urol., (1984), 131:430–433.
Pak et al., J. Clin. Pharmacol., (1984), 24:622–629.
Pak et al., J. Urol., 134:11–19.
Preminger et al., J. Urol., (1985), 134:20–23; 658–661.
Rutherford, Center Times, Aug. 1985.
Pak et al., Amer. J. Med., (1985), 79:284–288.
Pak et al., Ann. Int. Med., (1986), 104:33–37.
Pak et al., Kidney International, (1986), 30:422–428.
Pak and Peterson, Arch. Intern. Med., (1986), 146:863–867.
Packett et al., (date unavailable), pp. 1716–1720.

COMPOSITIONS AND METHODS OF TREATING CALCIUM RENAL STONES

This invention is a continuation-in-part of copending U.S. patent application Ser. No. 741,715, filed June 6, 1985, , now abandoned, which is a continuation of U.S. patent application Ser. No. 483,678, filed April 11, 1983, , now abandoned, both of which are incorporated by reference herein.

BACKGROUND OF THE INVENTION

The present invention relates to methods and compositions for medical treatment; and more particularly, this invention relates to methods and compositions for the treatment and prophylaxis of calcium renal stones.

Formation of stones within the urinary tract (clinically termed nephrolithiasis) represents a common health disorder. In the United States an estimated 5-10% of the population will develop urinary stones in their lifetime. Of these stones virtually all originate in the kidneys, while bladder stones are rarely encountered except in association with a foreign body. Nephrolithiasis, while usually not fatal, causes considerable suffering, morbidity and loss of work. Often it is a disease which recurs throughout a patient's lifetime.

The medical profession has become increasingly aware that recurrent formation of renal stones may be prevented by a variety of medical interventions in a significant number of patients at risk for nephrolithiasis. However, many treatment programs are used indiscriminately without regard for the particular cause for stone formation. For example, stones of renal origin may be broadly categorized on the basis of their chemical composition as those containing calcium, and those which do not. Calcareous renal stones account for 80-90% of stones, and are principally composed of calcium oxalate (dihydrate or monohydrate) and calcium phosphate (apatite or rarely brushite and whitlockite). Further, calcareous renal stones can be subdivided into physiological pathogenesis, for example hypercalciuria, hyperuricosuria, hyperoxaluria and hypocitraturia. Non-calcareous renal stones include those containing uric acid, cystine, or magnesium ammonium phosphate (struvite).

Notwithstanding the various etiologies attributed to renal stone formation, treatments have generally been randomly selected. Thus, orthophosphate and thiazide have been used in various forms of hypercalciuric as well as in normo-calciuric states, and allopurinol has been used in hyperuricosuria as well as in normouricosuria. With respect to non-calcareous renal stones, specifically uric acid lithiasis, an improved treatment program has virtually eradicated the incidence of this disease state. Unfortunately treatments effective for uric acid stones, specifically administration of sodium citrate and sodium bicarbonate, appear to potentiate formation of calcium stones, (see e.g. Sakhaee, Nicar, Hill, and Pak, "Contrasting Effects of Potassium Citrate and Sodium Citrate Therapies on Urinary Chemistries and Crystallization of Stone-Forming Salts", Kidney International, (V 24, pp. 348-351 (1983)), incorporated by reference herein).

Coincident with the recognition of the above, the present applicant advocates a more selective approach, in which specific treatments are chosen for particular causes of stone formation. This approach recognizes the heterogeneity of pathogenic background for nephrolithiasis and tailors treatment programs to ameliorate, correct or prevent the specific underlying derangement.

The teachings of Kopp et al. (U.S. Pat. No. 4,289,750) and Helbig et al. (U.S. Pat. No. 4,405,596) are related to the processes of the present invention and are incorporated by reference herein. These U.S. patents involve the administration of an alkali-acting substance, prototypically sodium bicarbonate, to increase plasma bicarbonate level and induce alkalotic volume contraction. Kopp et al. (U.S. Pat. No. 4,289,750) state that although alkaline-acting substances other than sodium bicarbonate may be used, the alkaline-acting substance "would be adapted to release sodium and bicarbonate ions." (col 5, lines 40-44). Kopp et al. (U.S. Pat. No. 4,289,750) further indicate that an appropriate dose regimen of alkali-acting substance would raise blood bicarbonate levels by a 4 to 5 mEq/l base excess value. As shown in Pak et al. (J. of Urol. vol. 134, pp 11-19, see Table 5 (1985)), incorporated by reference herein, an effective dose regimen of potassium citrate did not raise serum bicarbonate or $CO_2$ levels to more than a fraction of this extent. It is also mentioned in Kopp et al. (U.S. Pat. No. 4,289,750) that its oral preparations "--are highly effective in increasing urine volume when administered at correct minimum dosage levels--" (col. 7, lines $63 \geqq 65$). As shown later herein, particularly in Table I, administration of effective levels of potassium citrate induces but a minor and statistically non-significant increase in urine volume.

Both Kopp et al. (U.S. Pat. No. 4,289,750) and Helbig et al. (U.S. Pat. No. 4,405,596) focus primarily upon patients with altered function or renal insufficiency. These clinical syndromes, particularly renal insufficiency, are contraindicative of potassium citrate therapy according to the processes of the present invention because the potassium citrate-based therapy might lead to hyperkalemia.

The alkaline-acting substances of Kopp et al. and Helbig et al. may be combined with additional active agents. Kopp et al. (U.S. Pat. No. 4,289,750) state that potassemia (sic) may be corrected by including a potassium compound such as potassium chloride, potassium bicarbonate or potassium citrate in the oral preparations of that invention. This reference further states that prevention of kidney stone formation or elimination of kidney stones may be encouraged by "inclusion in oral preparations of substances such as alkali or alkali earth metal citrates, or inclusion of urea itself". Thus one condition (potassemia) may be corrected, it is taught, by addition of a salt such as potassium citrate. Another condition (kidney stone presence or formation), it is taught, may be alleviated by the creation of a state of alkalotic volume contraction with increased urine volume and then adding substances such an alkali or alkali earth metal citrate. There is no indication in Kopp et al. (U.S. Pat. No. 4,289,750) that, as described elsewhere herein, sodium citrate encourages calcareous kidney stone formation. Nor is there any indication in Kopp et al., that specifically potassium citrate, on the contrary, alleviates this condition, even in the absence of alkalotic volume contraction.

Helbig et al. (U.S. Pat. No. 4,405,596) state that, in their preparations containing alkaline-acting agents, cations other than sodium may be suitable but that sodium is preferred. It is indicated in Helbig et al. (U.S. Pat. No. 4,405,596), a continuation-in-part of Kopp et al. (U.S. Pat. No. 4,289,750), that alkali or alkali earth metal salts of citric acid may be used for prophylaxis and therapy of kidney stones. These salts are directed to be administered as 'additional active agents' in conjunction with an alkaline-acting substance (col 1, lines 35–48). Additionally, Helbig et al. (U.S. Pat. No. 4,405,596) state that "the novel and essential characteristic of the oral dosage form of the invention is that resorbable bicarbonate ions are formed or released only in the intestine of a subject" (col. 5 lines 36–39). This characteristic distinguished their 'alkaline-acting' agent from other substances such as metallic citrates which do not intestinally release resorbable bicarbonate. Specific metallic citrates mentioned included hexapotassium-hexasodium-heptacitrate-hydrate- and hexacalcium-hexasodium-heptacitrate-hydrate-complexes. As it may be seen from these descriptions, Kopp et al. (U.S. Pat. No. 4,289,750) and Helbig et al. (U.S. Pat. No. 4,405,596) provide no guidance to the discoveries inherent in the present invention involving the use of potassium citrate free of substantial sodium and bicarbonate-releasing capability in intestinal lumen to effect a new cure for calcareous kidney stones.

The results of the present invention described herein clearly demonstrate that the administration of potassium citrate (but not sodium citrate), unaccompanied by alkali-acting substances releasing intestinal bicarbonate, is an effective treatment for calcareous kidney stones. Thus, sodium citrate is ineffective for treatment of kidney stones and sodium bicarbonate or any other sodium salt in combination with potassium citrate would detract from the therapeutic effectiveness of the potassium citrate by converting the potassium citrate to sodium citrate by equilibrium and ionic interchange.

In an earlier study, Rudman et al.(N. Eng. J. Med. Vol. 303, pp 657–661 (1980)) described the oral administration of a "citrate punch" comprising sodium citrate and citric acid to patients with hypocitraturia. This reference showed no increase in urinary citrate when patients were treated only with the "citrate punch". It was found that the hypocitraturia was corrected only when the "citrate punch" administration was accompanied by an intramuscular injection of magnesium sulfate. Although Rudman et al. acknowledged that hypocitraturia may result from hypokalemia or acidosis, no suggestion of using potassium citrate for treatment of calcareous kidney stones was made.

SUMMARY OF THE INVENTION

The present invention provides a method and compositions useful for the treatment and prophylaxis of calcium renal stones in persons susceptible to such stone formations. The method involves administering compositions of potassium citrate to a patient afflicted with or susceptible to calcium renal stone formation.

DETAILED DESCRIPTION OF THE PREFERRED EMBODIMENTS

The invention will be described in terms of preferred embodiments which represent the best mode known to the applicant at the time of this application.

In-depth metabolic studies on the part of applicant has revealed the surprisingly unexpected and unobvious superiority of potassium citrate therapy over sodium alkali therapy in the management of nephrolithiasis. (Sakhaee et al., Kidney International, V 24, pp 348–352, (1983)). Specifically, in patients with both uric acid and calcium nephrolithiasis, potassium citrate therapy causes a greater decline in urinary calcium and a greater rise in urinary citrate. Urinary sodium increases with sodium citrate therapy but not with potassium citrate. No significant or consistent changes occur in urinary uric acid, phosphate or oxalate. With both treatments, urinary pH rises to about an equivalent degree.

As reflected by the above described changes, potassium citrate is effective in lowering urinary saturation of calcium oxalate, does not cause a rise in sodium urate saturation, and produces a rise in urinary inhibitor activity against calcium oxalate nucleation. In contrast, sodium citrate raises the saturation of sodium urate and increases formation calcium oxalate stones.

Moreover, in patients with uric acid lithiasis, treatment with sodium alkali is associated with calcium stone formation (Pak, et al., Kidney International, V 30, pp 422–428, (1986)). The substitution of potassium citrate for sodium citrate inhibits calcium stone formation.

Consistent with the clinical findings of applicant's research, potassium citrate therapy is useful in the prevention of uric acid or cystine lithiasis since it is a good alkalizing agent. More importantly, potassium citrate therapy averts the complication of calcium stone formations in patients afflicted with uric acid or cystine lithiasis (as contrasted with treatment with sodium alkali which may potentiate calcium stone formation). Further, potassium citrate therapy is effective in restoring normal citrate in patients with hypocitraturia linked calcium nephrolithiasis and coincidently inhibits and dissolves calcium stone formations. The ability to dissolve calcium stones is heretofore an unreported finding with any medical treatment; conventional alkali therapy has customerily been associated with formation of calcium stones as stated in textbooks, pointing to uniqueness of this invention. Coincidentally, thiazide treatment has been shown to cause hypocitraturia and recurrent calcium stone formation. Adding potassium citrate could prevent hypocitraturia and avert calcium stone formation, emphasizing another very novel finding of this invention.

Typically, a dosage range of 30-120 meq potassium citrate per day given in divided doses is effective in preventing and treating calcium renal stones in patients afflicted with or susceptible to calcium stone formation. Generally recognized solid or liquid pharmaceutical form such as tablets, capsules, effervescent tablets, chewable tablets, solutions or syrups, are acceptable in delivering potassium citrate.

Examples of medicinal formulations in accordance with the present invention include:

| Potassium Citrate Drink Mix | Percent (w/w) |
|---|---|
| Potassium Citrate, U.S.P. | 21.63 |
| Fructose, U.S.P. | 70.00 |
| Flavor | 2.37 |
| Citric Acid, U.S.P. | 5.00 |
| Calcium Phosphate, Tribasic, N.F. | 1.00 | to be dissolved in water (sufficient to produce 2 meq/ml) prior to patient administration.

| Potassium Citrate Tablet (5 meq) | mg/Tablet |
|---|---|
| Potassium Citrate, U.S.P. | 540.5 |
| Carnauba Wax, N.F. | 200.0 |
| Talc, U.S.P. | 40.0 |
| Magnesium Stearate, N.F. | 5.0 |

In addition, K-Lyte (Mead Johnson Pharmaceutical Division, Evansville, Ind.) a mixture of potassium bicarbonate and potassium citrate is useful in the methods prescribed by this invention. Another useful preparation may be a mixture of potassium bicarbonate or potassium carbonate and citric acid.

In order that the invention may be more clearly understood, preferred embodiments will be further described in terms of the following examples (updated since the original patent application), which should not be construed to limit the scope of this invention.

The data describing these examples have largely been published in peer-reviewed reputable medical journals since the original patent application, indicating novelty and importance of this invention. Potassium citrate has also been approved as a prescription drug by the FDA (Food and Drug Administration) for the treatment of calcium renal stones as described herein, further supporting uniqueness of the invention. (NDA No. 19,071 was granted to the inventor in July, 1985).

EXAMPLE I

Comparative Analysis of Potassium Citrate and Sodium Citrate Therapies

An important determinant for the formation of uric acid stones is the passage of uncommonly acid urine. The urinary pH in patients with uric acid lithiasis is typically less than the dissociation constant (pKa) of uric acid of 5.47; thus, their urinary environment is supersaturated with respect to uric acid. Because uric acid is unstable and more soluble at a higher pH, it has been customary to recommend alkalinization of urine for management of uric acid nephrolithiasis. Principally owing to their ready commercial availability, sodium rather than potassium salts of bicarbonate and citrate have been used as alkalinizing agents.

Although it may cause dissolution or inhibit formation of uric acid stones, sodium alkali therapy is often complicated by the development of calcium-containing renal stones (calcium phosphate and/or calcium oxalate). This study indicates that potassium alkali therapy may avert such a complication in uric acid lithiasis. Moreover, the treatment with potassium citrate has shown to correct hypocitraturia (low urinary citrate), a defect frequently encountered in calcium nephrolithiasis. Thus, these findings suggest that potassium alkali is also useful in the management of calcium urolithiasis associated with hypocitraturia.

Five patients with documented uric acid lithiasis, who developed calcium stone complication on sodium alkali treatment, participated in this study (Sakhaee, Nicar, Hill and Pak, Kidney International, V 24, pp 348-352, (1983)). All subjects had adequate endogenous creatinine clearance, ranging from 75-130 ml/min. None of the participating subjects suffered from hyperkalemia, fluid retention, urinary tract infection, or urinary tract obstruction during the study. Among patients with uric acid lithiasis, one suffered from gout. None had chronic diarrheal syndrome.

The study comprised three phases, consisting of control phase (no drug), potassium citrate phase, and sodium citrate phase, conducted in random order. The dosage of the two forms of alkali were the same (60 mg/day in three divided doses orally). All other drugs were withheld during the study. Each phase was four weeks in duration. After three weeks of stabilization in an outpatient setting, patients underwent an inpatient evaluation during the last week.

During each inpatient evaluation, subjects were maintained on a constant metabolic diet with a daily composition of 400 mg calcium, 800 mg phosphorous, 100 meq sodium, 60 meq potassium and sufficient fluid to ensure approximately two liters of urine daily for the entire study period of six days. After three days of stabilization, urine was collected daily in 24-hour pools during last three days for total volume, pH, calcium, oxalate, phosphorous, sodium, potassium, magnesium, ammonium, citrate, sulfate, and uric acid; relative saturation ration (RSR) of monosodium urate and monopotassium urate; activity product ration (APR) of brushite ($CaHPO_4.2H_2O$) and calcium oxalate; and formation product ration (FPR) of brushite and calcium oxalate.

TABLE I

Effect of Alkali Therapies on Urinary Chemistries and Crystallization in Patients with Uric Acid Lithiasis

| | Control | Potassium Citrate | Sodium Citrate |
|---|---|---|---|
| Total Volume ml/day | 2456 ± 290 | 2525 ± 359 | 2669 ± 296 |
| pH | 5.35 ± 0.18 | 6.68 ± 0.14 | 6.73 ± 0.20 |
| Calcium, mg/day | 154 ± 47 | 99 ± 23 | 139 ± 24 |
| Citrate, mg/day | 398 ± 119 | 856 ± 103 | 799 ± 89 |
| Uric Acid, mg/day | 417 ± 121 | 522 ± 171 | 512 ± 132 |
| Activity Product Ratio (APR) | | | |
| Calcium Oxalate | 3.21 ± 0.96 | 1.69 ± 0.76 | 2.21 ± 0.63 |
| Brushite | 0.04 ± 0.03 | 0.74 ± 0.22 | 1.17 ± 0.44 |

TABLE I-continued

Effect of Alkali Therapies on Urinary Chemistries and
Crystallization in Patients with Uric Acid Lithiasis

|  | Control | Potassium Citrate | Sodium Citrate |
|---|---|---|---|
| Formation Product Ratio (FPR) | | | |
| Calcium Oxalate | 16.1 ± 5.6 | 22.2 ± 6.6 | 14.1 ± 5.3 |
| Relative Saturation Ratio (RSR) | | | |
| Monosodium Urate | 0.51 ± 0.20 | 0.95 ± 0.33 | 1.45 ± 0.44 |
| Monopotassium Urate | 0.05 ± 0.02 | 0.33 ± 0.07 | 0.12 ± 0.04 |

A review of the above results indicates that, in patients with uric acid lithiasis, both alkali therapies caused a significant decline in urinary saturation (APR) of calcium oxalate; however, the decline was more prominent during potassium citrate therapy than during sodium alkali therapy. Thus, urinary saturation of calcium oxalate declined during alkali therapies, more so when potassium citrate was given. Urinary APR (saturation) of brushite increased during both alkali therapies; the rise was more prominent during sodium citrate therapy. Urinary environment became supersaturated (APR>1) with respect to brushite during sodium alkali treatment, whereas it remained undersaturated when potassium citrate was given.

The urinary FPR (a measure of inhibitor activity) of calcium oxalate rose significantly during oral potassium citrate treatment. Thus, spontaneous precipitation of calcium oxalate commended at a higher lever of supersaturation when potassium citrate was given. However, FPR of calcium oxalate did not change significantly during sodium citrate therapy. The difference in FPR between the two alkali phases was significant. In 2 of 5 patients, FPR decreased by more than 30%; thus, spontaneous precipitation was facilitated in some patients.

The saturation of monosodium urate (RSR) rose significantly during both alkali phases, more so during sodium citrate therapy. The urinary environment became supersaturated with respect to monosodium urate during sodium citrate therapy, but remained undersaturated when potassium citrate was given. The saturation of monopotassium urate (RSR) increased significantly during both alkali treatments, but more so during potassium citrate therapy.

The results of this study disclose that both potassium citrate and sodium citrate are effective in the prevention of uric acid lithiasis since both alkali increased urinary pH (and therefore increased the solubility of uric acid).

However, the results suggest that sodium citrate does not prevent the complication of calcium nephrolithiasis when given to patients with uric acid stones. It might cause this complication because of increased urinary saturation of calcium phosphate, and in some patients when the effect of monosodium urate-induced calcium oxalate crystallization overrides the inhibitory action of citrate.

In contrast to the action of sodium citrate, potassium citrate at an equimolar dosage significantly reduced urinary calcium excretion while increasing urinary citrate excretion. This study therefore indicated that potassium citrate, unlike sodium citrate, prevent the complication of calcium oxalate nephrolithiasis when given to patients with uric acid lithiasis. This prevention involved reducing urinary saturation by calcium oxalate and inhibiting spontaneous precipitation of calcium oxalate. The potassium citrate-containing compositions of the present invention preferably comprise less than about ten weight percent sodium salts and more preferably are substantially free of sodium salts.

EXAMPLE II

Potassium Citrate is Effective in Preventing Calcium Stone Formation (in 5 Patients with Uric Acid Stones) Caused by Sodium Alkali Therapy Detailed case reports were obtained in 5 patients with uric acid nephrolithiasis showing different response between sodium alkali and potassium alkali treatment (Pak et al., Kidney International, V 30, pp 422-428, (1986)). Before treatment, they had surgically removed or spontaneously passed stones which were pure uric acid in composition. When sodium alkali was given (as bicarbonate or citrate, 60-118 meq/day, in one case as a mixture with potassium alkali), new stone formation continued in 4 patients, and a radiolucent (uric acid) stone became "calcified" in the remaining patient. The stone analysis disclosed calcium oxalate in 5 patients and calcium phosphate in three patients.

Figure 1:
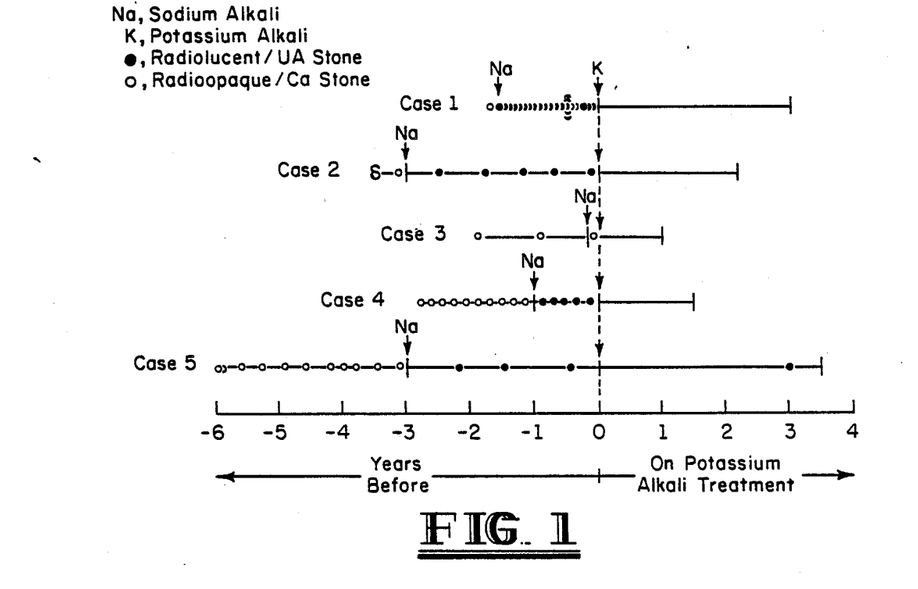
FIG. 1 shows the effect of alkali therapy on new stone formation and pre-existing stones in patients with uric acid nephrolithiasis.

When potassium citrate (in 4 cases) or potassium bicarbonate (in 1 patient) was administered in place of the sodium alkali over 1 to 3.5 years (at a dosage of 60-80 meq/day, no new stones were formed (one passed by case 5 was a preexisting stone) (FIG. 1).

In summary, five patients with known uric acid stones had a complication of calcium stones during sodium alkali therapy (alone or in combination with potassium alkali). Both calcium and uric acid stone formation ceased when patients were treated with potassium citrate (or bicarbonate).

EXAMPLE III

Figure 2:
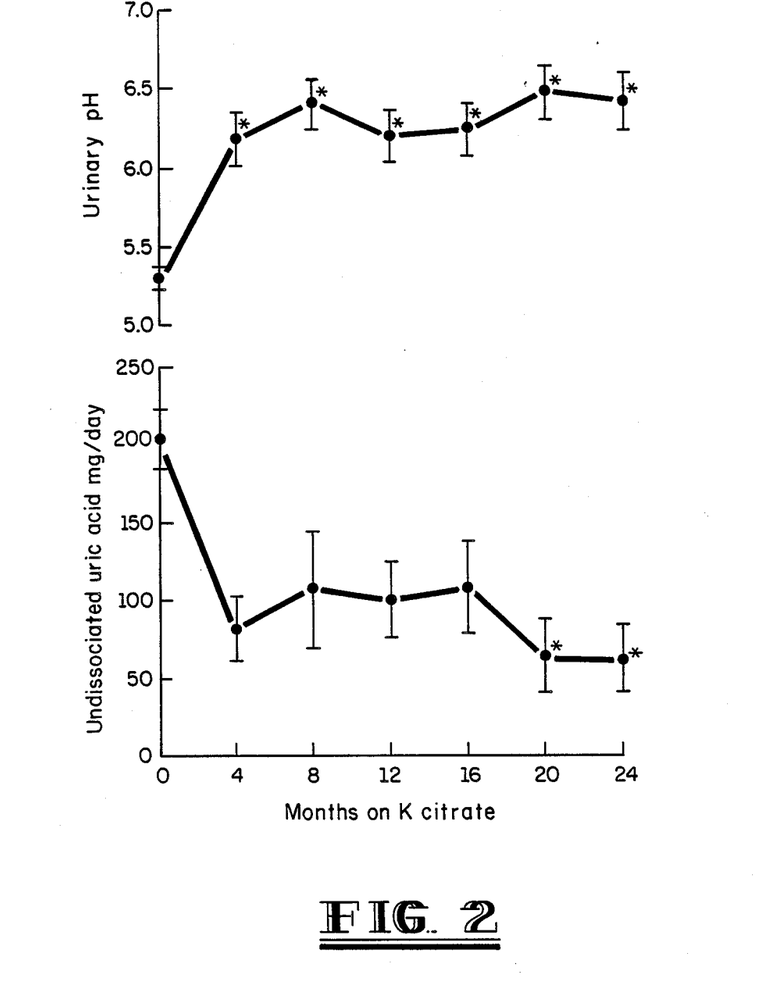
FIG. 2 shows the effect of potassium citrate treatment on urinary pH and undissociated uric acid. Significant difference from pre-treatment value produced by treatment is shown by * for $p < 0.05$.
Figure 3:
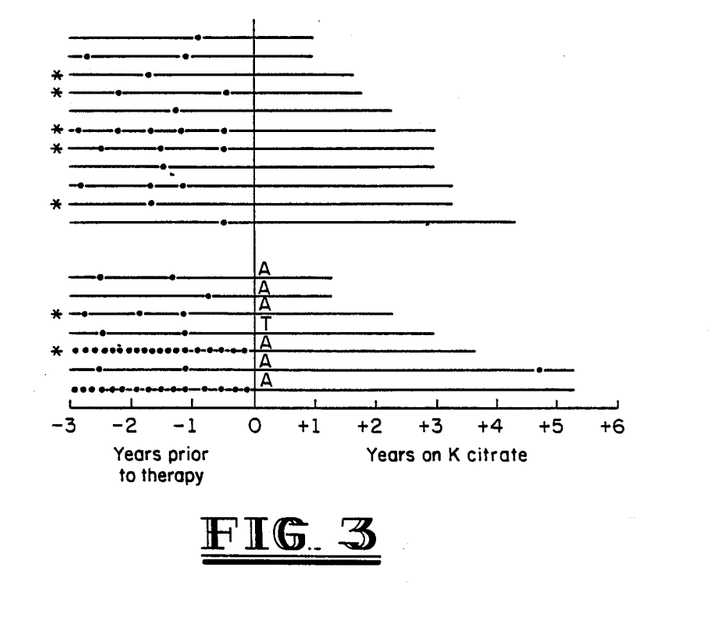
FIG. 3 shows the effect of potassium citrate treatment on new stone formation. Each circle represents new stone formation. Each line indicated study in a separate patient. Asterisk denotes patients with pre-existing stone when the treatment with potassium citrate was begun. The bottom seven patients took potassium citrate concurrently with allopurinol (A) or thiazide (T).

Long-Term Prevention of Stone Formation by Potassium Citrate Therapy in Patients with Uric Acid Nephrolithiasis with or without Complication of Calcium Renal Stone Eighteen patients with uric acid nephrolithiasis (six with uric acid stones alone and 12 with both uric acid and calcium stones) underwent long-term treatment (1-5.33 years) with potassium citrate (30-80 meq/day) (Pak, et al, Kidney International, V 30, pp 422-428, (1986)), urinary pH increased from low (5.3±0.31) to normal (6.19 to 6.46) during treatment (FIG. 2). Consequently, the urinary content of undissociated uric acid, which was high to begin with, decreased to the normal range during treatment, making uric acid precipitation unlikely (FIG. 2). Urinary citrate rose from 503±225 mg/day to 852-998 mg/day. Urinary saturation of calcium oxalate declined with potassium citrate treatment. New stone formation (either uric acid or calcium stone) declined from 1.20±1.68 stone/patient year to 0.01+0.04 stones/patient year (FIG. 3). 94.4% of patients did not form further stones.

These results, showing that potassium citrate is effective in the management of uric acid lithiasis presently with or without calcium stones, are the basis for the FDA approval of potassium citrate as a prescription drug for this condition in July, 1985.

The above observation has since been confirmed by Dr. Nector Tomyez (endocrinologist) and Dr. Richard Lewis (urologist) who have written to the inventor's group (letters available upon request).

EXAMPLE IV

Potassium Citrate Therapy is Effective in Dissolving Existing Calcium Containing Renal Stones Prior to institution of potassium citrate therapy, 33 patients had pre-existing radiopaque calculi (calcium stones) visualized on abdominal roentgenograms (Pak et al., Trans. Assoc. Amer. Physic, V 96, pp 294–305, (1983)). Repeat examination after 8 months to 2 years of potassium citrate therapy showed a reduced number of stones in 14 patients. In 4 of them, this reduction could be attributed to the passage of stones. However, there were fewer stones visualized in 6 patients even though they did not remember passing stones. In the remaining patients, the number of stones passed could not entirely account for the reduced number of stones.

Thus, long-term potassium citrate treatment dissolved calcium stones located in kidneys of patients with stones. There is no prior known documented report of dependably dissolving calcium stones by any medical treatment.

EXAMPLE V

A Case History Showing Dissolution of Calcium Stones by Potassium Citrate Therapy A 62-year-old white woman with incomplete renal tubular acidosis passed approximately 400 stones during the preceding three years, as often as one a day in recent months. Stones were composed of calcium phosphate and calcium oxalate. Urinary citrate was very low at 34 mg/day. On potassium citrate therapy (20 meq four times/day), urinary citrate increased to 333–376 mg/day.

She passed only eight stones during twenty months of treatment. Abdominal X-ray taken at fourteen months of treatment disclosed marked changes. Before treatment, she had numerous radiopaque calculi in both kidneys. After treatment, stones in the mid and lower pole of right kidney and mid-portion of left were no longer seen.

EXAMPLE VI

Potassium Citrate Effectively Prevents New Stone Formation in Patients with Distal Renal Tubular Acidosis Distal renal tubular acidosis is a common cause of hypocitraturia and intractible calcium nephrolithiasis. The effect of oral potassium citrate therapy in 9 patients with incomplete distal venal tubular acidosis was examined (Preminger et al., J. Urology, V 134, pp 20–23 (1985)). Potassium citrate (60–60 meq/day in divided doses) significantly increased urinary citrate, and lowered urinary calcium. Thus, the urinary saturation of calcium oxalate significantly decreased during treatment while that of brushite (Ca phosphate) did not change.

During a mean treatment period of 34 months, none of nine patients formed new stones, although the same patients had formed an average of 39.3 stones/year during the three years prior to treatment.

Thus, potassium citrate therapy was effective in correcting biochemical abnormalities and preventing recurrent calcium stone formation in patients with distal renal tubular acidosis. The novelty of this finding was supported by the acquisition, by the inventor, of a new drug application from the FDA for this condition in July, 1985.

Recent studies by the inventor's laboratory in 6 patients with distal renal tubular acidosis indicated that sodium citrate was not as advantageous a treatment agent as was potassium citrate. Urinary calcium remained high at 216 mg/day (from a control value of 214 mg/day) during sodium citrate (60 meq/day) treatment, whereas it decreased to 178 mg/day during potassium citrate (60 meq/day) treatment. Urinary citrate increased to a lesser degree (493 mg/day from 253 mg/day) during sodium citrate therapy, then during potassium citrate treatment (575 mg/day). The urinary saturation of calcium phosphate rose by 37% during sodium citrate treatment, whereas it was unaltered by potassium citrate treatment. Thus, sodium alkali therapy may not be an effective in, or may even exaggerate, calcium stone formation in renal tubular acidosis.

EXAMPLE VII

Figure 4:
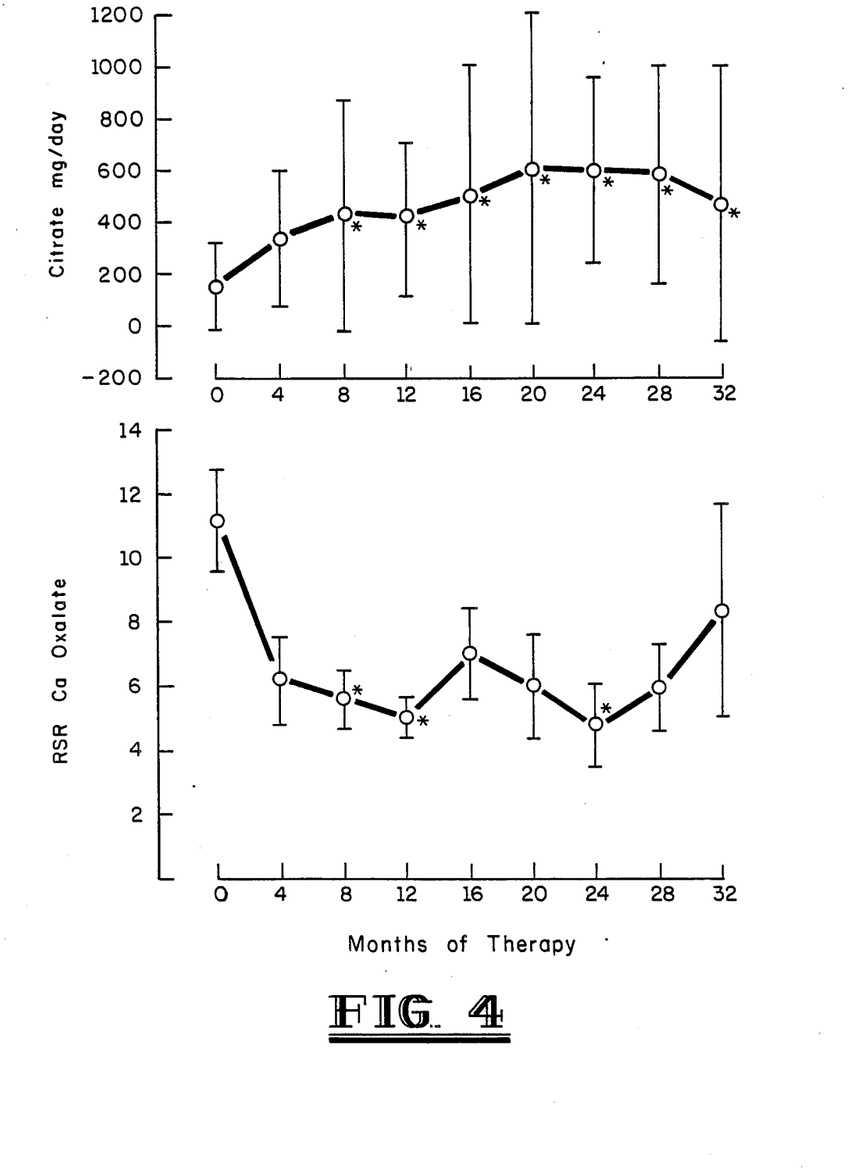
FIG. 4 shows the effect of potassium citrate therapy on urinary citrate and relative saturation ratio of calcium oxalate. Bars indicate mean ±SEM. * = $p < 0.05$.
Figure 5:
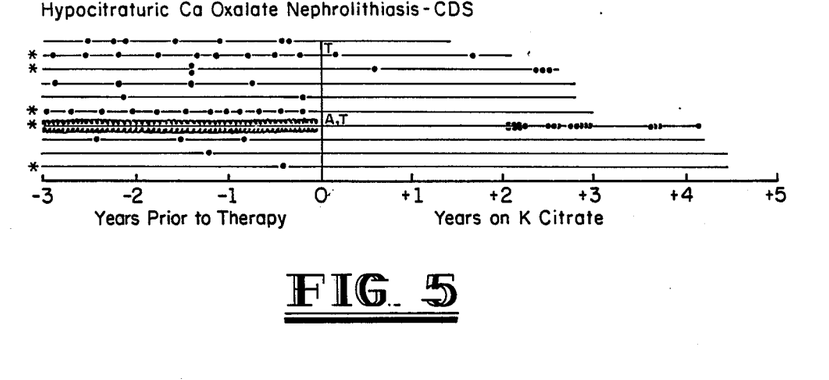
FIG. 5 shows the effect of potassium citrate on new stone formation. Each line represents study in a separate patient. Asterisk before the line indicates presence of pre-existing renal stone(s). Each point shows new stone formation. A=allopurinol, T=thiazide.

Potassium Citrate Effectively Prevents New Stone Formation in Patients with Chronic Diarrheal Syndrome Long-term effects of potassium citrate therapy (60–80 meq/day in 3–4 divided doses) on urinary biochemistry and on stone formation were examined in 10 patients with calcium oxalate nephrolithiasis due to chronic diarrheal syndrome (regional enteritis, jejuno-ileal bypass surgery, partial gastrectomy or ulcerative colitis). Urinary citrate was low (<320 mg/day) in 9 patients, and urinary oxalate was high in 4 patients. Potassium citrate therapy caused a sustained increase in urinary citrate from $148\pm154$ (SD) mg/day to 333–615 mg/day, and produced a sustained reduction in urinary saturation (RSR) of calcium oxalate (FIG. 4). During a mean treatment period of 3.2 years, stone formation rate declined from $4.69\pm10.12$ to $0.71\pm1.44$ stones/patient year ($p<0.01$), and 7 patients (70%) remained stone-free (FIG. 5). Thus, potassium citrate represents an important therapeutic modality in the management of hypocitraturic calcium oxalate nephrolithiasis due to chronic diarrheal syndrome.

The failure of Rudman et al., N. Engl. J. Med., V 303, pp 657–661 (1980)) to show a significant rise in urinary citrate with sodium citrate-citric acid in patients with hypocitraturia of gastrointestinal origin emphasizes the uniqueness of potassium citrate action.

EXAMPLE VIII

Potassium Citrate Therapy Prevents Hypocitraturia Caused by Thiazide Treatment of Hypercalciuric Calcium Nephrolithiasis Thirteen patients with hypercalciuric calcium renal stones were treated with thiazide, a treatment widely used for this condition because of its ability to lower urinary calcium. Even though urinary calcium decreased from $303\pm119$ mg/day to $193\pm$mg/day on treatment, they continued to form kidney stones (6.62 to 5.12 stones/patient year) (Pak et al., Amer. Jrnl. of Med., V 79, pp 284–288 (1985)).

Because they had hypocitraturia (250 mg/day), potassium citrate (30–60 mq/day in divided doses) was added to the ongoing treatment program. During combined treatment with thiazide and potassium citrate, urinary pH significantly rose and normal urinary citrate was restored. Ten patients stopped forming stones.

Figure 6:
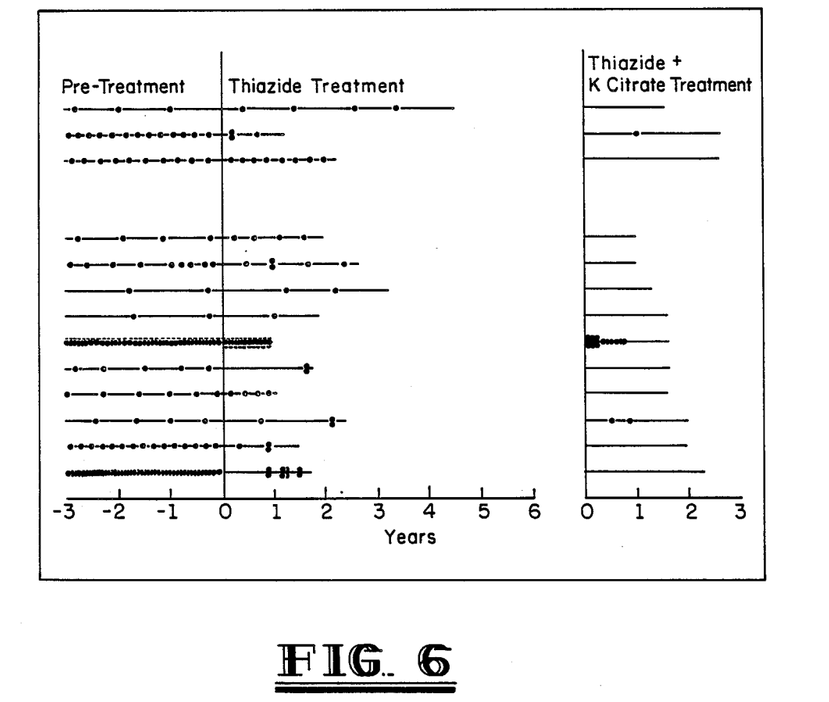
FIG. 6 shows the effect of thiazide treatment and thiazide and potassium citrate treatment on new stone formation. Each line represents the study in a separate patient. Each point indicates new stone formation. Combined thiazide and potassium citrate treatment was begun immediately after thiazide treatment.

Stone formation significantly declined from 5.12 stones/patient year to 0.05 stones/patient year (FIG. 6).

This novel discovery, showing effectiveness of potassium citrate in patients who continue to form stones on thiazide, was the basis for the NDA approval acquired by the inventor for potassium citrate to be used concurrently with thiazide in hypercalciuric nephrolithiasis. This finding has been confirmed by cooperative studies of Dr. Donald Griffith at Houston (a part of NDA 19,071 report, available upon request).

In that study, Dr. Griffith studied 29 patients with hypercalciuric calcium nephrolithiasis who continued to form stones on thiazide therapy. Potassium citrate was added to the ongoing thiazide treatment program. None of 29 patients formed any stone on combined thiazidepotassium citrate treatment. New stone formation declined from 0.64 stones/patient year to zero.

EXAMPLE IX

Potassium Citrate is Effective in Preventing Stone Formation in Patients with Idiopathic Hypocitraturic Calcium Oxalate Nephrolithiasis The effects of long-term treatment with potassium citrate (30–80 meq/day) were examined in 37 patients with idiopathic-hypocitraturic calcium oxalate nephrolithiasis, in whom the main causes of hypocitraturia (renal tubular acidosis, chronic diarrhea or hypokalemia) were excluded or considered unlikely (Pak, et al., Annuls of Internal. Med., V 104, pp 33–37 (1986)).

Figure 7:
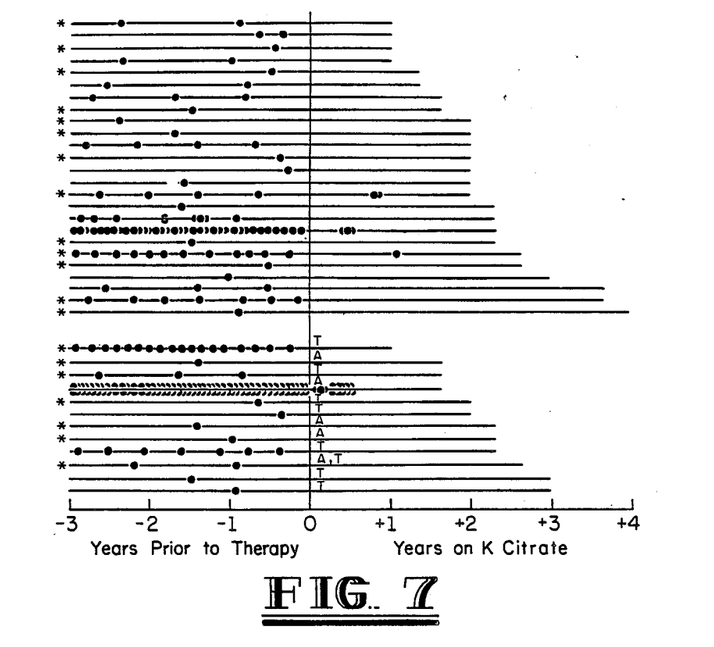
FIG. 7 shows the effect of potassium citrate therapy on new stone formation. Each line represents one patient. An asterisk before the line indicates presence of preexisting stone(s). Each point shows new stone formation. A=allopurinol; T=thiazide.

Potassium citrate treatment produced a sutained increase in urinary citrate excretion from an initially low value (223 to 253 mg/day) to within normal limits (470 to 620 mg/day). Urinary pH rose significantly and was maintained at 6.5 to 7.0. Along with these changes, urinary saturation of calcium oxalate significantly declined to normal. Further stone formation ceased in 89.2% of patients during treatment, and new stone formation rate declined from 2.11 stones/patient year to 0.28 stones/patient year (FIG. 7).

This indication for potassium citrate treatment was again approved by the FDA in awarding an NDA to the inventor in July, 1985.

EXAMPLE IX

Prevention of Calcium Stone Formation by Potassium Citrate in Patients with Hyperuricosuric Calcium Oxalate Nephrolithiasis Previous examples, all updated and validated by publications in peer-reviewed journals, were contained or described, at least in a preliminary form, in the original patent application (U.S. Ser. No. 483,678). However, this Example represents a new finding heretofore not specifically mentioned (published in May, 1986).

Calcium renal stone formation in patients with high urinary uric acid (hyperuricosuric calcium oxalate nephrolithiasis) is believed to be due to the induction of the crystallization of calcium oxalate by monosodium urate. The present Example shows that citrate, when added to a synthetic solution metastably supersaturated with respect to calcium oxalate, inhibited heterogeneous nucleation (induction of crystallization) of calcium oxalate by monosodium urate (Pak et al., Archive Internal. Med., V 146, pp 863–867, (1986)).

Figure 8:
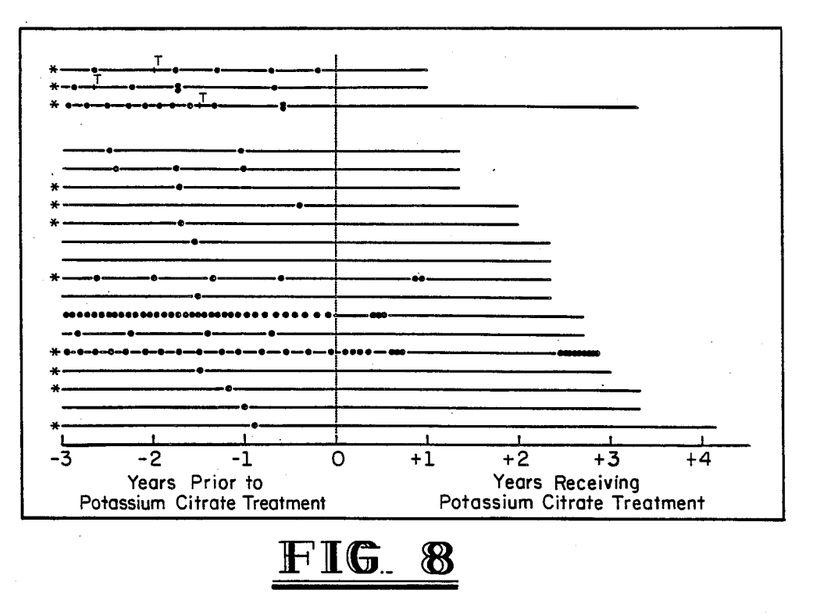
FIG. 8 shows the effect of long term treatment with potassium citrate on stone formation. Each line represents separate patient; each circle, new stone episode. Asterisk before line indicates preexisting stones before institution of treatment. For first three patients, thiazide treatment is shown by T.

Long-term treatment with potassium citrate (60–80 meq/day) was undertaken to determine whether induced hypercitraturia could prevent calcium oxalate stone formation in 19 patients with hyperuricosuria. The treatment produced a sustained rise in urinary pH and citrate, and a reduction in urinary saturation of calcium oxalate and in the urinary content of undissociated uric acid. Stone formation declined from 1.55/patient year to 0.38/patient year and ceased in 16 of 19 patients (FIG. 8). This finding, showing effectiveness of potassium citrate in preventing calcium stone formation in patients with hyperuricosuria, represents a heretofore unreported unique demonstration.

While the methods of this invention have been described in terms of preferred embodiments, it will be apparent to those of skill in the art that various changes may be made in the methods disclosed without departing from the scope of the invention, which is defined by the following claims.

What is claimed is:

1. A method for prevention of calcium renal stone formation in a patient susceptible to such stone formation and for dissolution of calcium renal stones and prevention of further calcium renal stone formation in a patient afflicted with calcium renal stones, the method comprising:

administering the patient a daily oral dosage of a composition consisting essentially of potassium citrate, the daily oral dosage containing potassium citrate in an amount between about 30 meq and about 120 meq.

2. The method of claim 1 wherein the patient susceptible to calcium renal stone formation is afflicted with uric acid nephrolithiasis.

3. The method of claim 1 wherein the patient is defined further as undergoing thiazide therapy.

4. The method of claim 3 wherein the thiazide therapy is associated with hypocitraturia.

5. The method of claim 1 wherein the patient is defined further as being associated with renal tubular acidosis.

6. A method for dissolution of calcium renal stones in a patient, the method comprising:

diagnosing that a patient is afflicted with calcium renal stones; and administering to the patient a daily oral dosage of a composition consisting essentially of potassium citrate, the daily dosage containing potassium citrate in an amount between about 30 meq and about 120 meq.

7. The method of claim 1 or 6 wherein the composition is defined further as being a liquid pharmaceutical composition, or an effervescent tablet preparation.

8. The method of claim 1 or 6 wherein the daily oral dosage is defined further as comprising two to four equally divided doses.

9. The method of claim 1 or 6 wherein the oral dosage is defined further as being in a tablet form.

10. The method of claim 1 or 6 wherein the oral dosage comprises a pharmaceutically acceptable carrier which slowly releases soluble potassium citrate.

11. The method of claim 10 wherein the oral dosage comprises carnauba wax.

12. The method of claim 1 or 6 wherein the composition is substantially free of sodium salts.

13. The method of claim 1 or 6 wherein the patient afflicted with calcium renal stones or susceptible to calcium renal stone formation is defined further as having hypercuricosuria.

* * * * *

UNITED STATES PATENT AND TRADEMARK OFFICE
CERTIFICATE OF CORRECTION

PATENT NO. : 4,888,182

DATED : December 19, 1989

INVENTOR(S) : Charles Y. C. Pak

It is certified that error appears in the above-identified patent and that said Letters Patent is hereby corrected as shown below:

In claim 5, column 12, line 37, delete the term "being associated with" and substitute the term --having--.

Signed and Sealed this

Fourteenth Day of January, 1992

Attest:

HARRY F. MANBECK, JR.

*Attesting Officer*    *Commissioner of Patents and Trademarks*